United States Patent [19]

Ullman et al.

[11] 4,191,613
[45] * Mar. 4, 1980

[54] MALATE DEHYDROGENASE CONJUGATES FOR ENZYME IMMUNOASSAYS

[75] Inventors: Edwin F. Ullman, Atherton; Kenneth E. Rubenstein, Menlo Park, both of Calif.

[73] Assignee: Syva Company, Palo Alto, Calif.

[*] Notice: The portion of the term of this patent subsequent to Dec. 3, 1991, has been disclaimed.

[21] Appl. No.: 760,499

[22] Filed: Jan. 19, 1977

Related U.S. Application Data

[63] Continuation-in-part of Ser. No. 722,964, Sep. 13, 1976, Pat. No. 4,067,774, which is a continuation of Ser. No. 481,022, Jun. 20, 1974, abandoned, which is a continuation-in-part of Ser. No. 304,157, Nov. 6, 1972, Pat. No. 3,852,157, which is a continuation-in-part of Ser. No. 143,609, May 14, 1971, abandoned.

[51] Int. Cl.$^2$ ............................ G01N 31/14; C07G 7/02
[52] U.S. Cl. ............................................ 435/188; 435/7
[58] Field of Search ........................... 195/63, 103.5 A

[56] References Cited

U.S. PATENT DOCUMENTS

| | | | |
|---|---|---|---|
| 3,850,752 | 11/1974 | Schuurs et al. | 195/63 |
| 3,852,157 | 12/1974 | Rubenstein et al. | 195/63 |

*Primary Examiner*—Alvin E. Tanenholtz
*Attorney, Agent, or Firm*—Bertram I. Rowland

[57] ABSTRACT

Novel conjugated enzyme compositions are provided for use in homogeneous enzyme immunoassays. A wide variety of compounds, particularly drugs, including drugs of abuse, drugs used in repetitive therapeutic applications, hormones, and the like, are conjugated to malate dehydrogenase. The resulting products have a high turnover rate, so as to provide a high multiplication factor when employed in a homogeneous immunoassay, have long storage lives, and allow for the accurate and sensitive detection of compounds of interest.

18 Claims, No Drawings

MALATE DEHYDROGENASE CONJUGATES FOR ENZYME IMMUNOASSAYS

CROSS-REFERENCE TO RELATED APPLICATIONS

This application is a continuation-in-part of application Ser. No. 722,964, filed Sept. 13, 1976, now U.S. Patent No. 4,067,774, which was a continuation application of divisional application Ser. No. 481,022, filed June 20, 1974, now abandoned, which application was a divisonal of continuation-in-part application Ser. No. 304,157, filed Nov. 6, 1972, now U.S. Pat. No. 3,852,157, which in turn was a continuation-in-part of application Ser. No. 143,609, filed May 14, 1971, now abandoned.

BACKGROUND OF THE INVENTION

1. Field of the Invention

Immunoassays have shown themselves to be extremely versatile in allowing for methods to determine the presence of a particular substance, even when a wide variety of other materials of similar or different structure are present in the unknown sample. The immunoassays rely on the ability of an antibody to specifically detect or bind to an haptenic or antigenic organic compound, while not interacting with other compounds. The divalent nature of the antibody and its high molecular weight, 150,000 or greater, allow for a sufficient change in the compound or environment of the compound to permit a discrimination between a compound which is bound and a compound which is not bound to antibody. Among various immunoassays involving antibodies are radioimmunoassay, spin immunoassay, available under the trademark FRAT, supplied by Syva Company, homogeneous enzyme immunoassay, available under the trademark EMIT, supplied by Syva Company, and hemeagglutination.

The enzyme immunoassay is extremely versatile in permitting spectrophotometric determinations. The immunoassay employs an enzyme to which the organic compound to be determined is conjugated. The organic compound is conjugated at a position where when bound to antibody, the activity of the enzyme is substantially reduced. To the extent that the unknown sample contains the same organic compound, the amount of antibody available for binding to the organic compound conjugated to the enzyme is reduced. Therefore, by analyzing for enzymatic activity a significant increase in enzymatic activity over the enzymatic activity in the absence of the unknown indicates the presence of the organic compound in the unknown.

The sensitivity of the homogeneous enzyme immunoassay is based to a substantial degree on the activity of the enzyme when conjugated and the degree of inhibitability when antibody is bound to the organic compound conjugated to the enzyme. It is, therefore, desirable to have an enzyme which not only has a high turnover rate initially, but retains a substantial proportion of this turnover rate after conjugation, and is strongly inhibited when antibody is bound to the organic compound which is conjugated to the enzyme. Also, the enzyme should allow for strong specific binding of antibody to the conjugated organic compound.

2. Description of the Prior Art

An homogeneous enzyme immunoassay system has been sold under the trademark EMIT employing haptens conjugated to lysozyme, where the enzymatic activity is determined by the reduction in turbidity as a result of lysis of bacterial walls. Numerous publications concerning the system have issued since June of 1971, see for example, Rubenstein, et al, Biochem. & Biophysical Res. Comm. 47 846 (1972). U.S. Pat. No. 3,654,090 teaches a heterogeneous immunoassay employing such enzymes as peroxidase and amyloglucosidase.

SUMMARY OF THE INVENTION

Ligand, usually haptenic, conjugates to malate dehydrogenase are provided for employment in homogeneous enzyme immunoassays to provide high sensitivity in detecting extremely small amounts of organic materials. One or more of the ligands is conjugated by relatively short chains or linking groups to the malate dehydrogenase to provide a product which can be used in a homogeneous enzyme immunoassay. With most ligands, the resulting conjugate retains a substantial proportion of the original enzyme activity and has a high degree of inhibitability, usually in excess of 50% of the activity of the conjugated malate dehydrogenase. The linking chains conveniently employ a non-oxocarbonyl group or a covalent bond to saturated carbon as the linking group to the enzyme.

DESCRIPTION OF THE SPECIFIC EMBODIMENTS

Ligand conjugated malate dehydrogenase is provided having from about 1 to 18, usually from about 2 to 14, and more usually from about 2 to 12 ligands, normally the majority of all the ligands being bonded to amino groups, particularly of lysine. The ligands will normally have molecular weights of at least about 125 and generally not exceeding 6,000, usually not exceeding 1,200, and frequently not exceeding 800 molecular weight. The ligands will have at least one heteroatom and may have two or more heteroatoms, which will normally be oxygen, nitrogen, and sulfur, although halogen, particularly chlorine and iodine may also be present, as well as metal counterions e.g. alkali metals of Group I. The ligands for the most part will be naturally occurring physiologically active compounds and synthetic drugs which are modified to the extent necessary for conjugation to the malate dehydrogenase.

The enzyme conjugates of this invention will for the most part have the following formula:

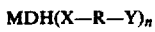

$$MDH(X-R-Y)_n$$

wherein:

MDH intends malate dehydrogenase; n indicates the average number of groups bounded to the MDH and will generally be in the range of 1 to 18, more usually in the range of 2 to 14, and particularly in the range of 2 to 12;

R is a bond or a hydrocarbon (aliphatic, alicyclic or aromatic), particularly aliphatic, linking group, either branched or straight chain, of from 0 to 1 rings and of from 1 to 8 carbon atoms, more usually of from 1 to 6 carbon atoms, and preferably of from 1 to 4 carbon atoms, usually having from 0 to 1 site of aliphatic unsaturation e.g. ethylenic, and more usually aliphatically saturated, or substituted hydrocarbon group having from 0 to 3 heteroatoms, more usually 0 to 2 heteroatoms, which are oxygen, sulfur and nitrogen, more usually oxygen and nitrogen (atomic number 7–8);

Y is a ligand of at least 125 molecular weight, usually not greater than 1,000 molecular weight, more usually not greater than 800 molecular weight, and generally not exceeding 650 molecular weight, and has at least one common epitope to a naturally occurring physiologically active compound or synthetic drug, usually differing from the naturally occurring physiologically active compound or synthetic drug by replacement of a hydrogen or modification of a functionality such as an olefin, oxo or the like, to provide a site for bonding of R to the ligand; and X is a bond, a non-oxocarbonyl group, including the nitrogen and sulfur analogs thereof, i.e. imino and thiocarbonyl, or diazo, when R is arylene, aralkylene or a bond and the nitrogen of the diazo group is bonded to an aromatic annular carbon atom.

X may be bonded to R through carbon or a heteroatom, particularly nitrogen. Since sulfur bonds and certain oxygen bonds, e.g. esters will tend to be reactive, these will usually be avoided. Oxygen will normally be present in the linking group as a carbonyl (oxo or non-oxo) or oxyether. Sulfur will normally be present in the linking group as thiocarbonyl or thioether. Nitrogen will normally be present in the linking group as tertiary or quaternary amino, diazo or bonded to a non-oxocarbonyl e.g. amido, including the amino and thioanalogs thereof.

Usually, when R is aromatic (aromatic includes arylene, aralkylene or alkarylene), R will be bonded to Y through a heteroatom, particularly ethereal oxygen, i.e. oxy. R groups of particular interest are methylene or polymethylene, i.e. $(CH_2)_p$, where p is an integer in the range of 1 to 6, alkyleneoxyalkylene, i.e., $(CH_2)_qO(CH_2)_r$, where q and r ar the same or different and are integers in the range of 1 to 3, there being at least two methylene groups between heteroatoms, or $(CH_2)_sNH$, where s is an integer in the range of 1 to 6, usually 1 to 4, there being at least two methylene groups between heteroatoms.

When X is other than a bond, X will normally have one of the following formulae:

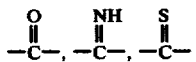

and will preferably be either the oxygen or the imino non-oxocarbonyl.

The groups for —R—X— will include ethylene, propylene, butylene, hexylene, phenylene, p-benzylylene, α-carboxymethine, carbamoylmethylene (—NHCOCH$_2$—), iminoxyacetyl (=NOCH$_2$CO—), thioacetyl, p-oxybenzyl, maleidioyl, succindioyl, oxoethylene (—OCCH$_2$—), 1-oxobutylene (—OCCH$_2$CH$_2$CH$_2$), ethyleneoxyacetyl, propyleneoxyacetyl, N-methyl 3-aza-1-imino-pentylene-(—(NH=C)—CH$_2$N(CH$_3$)CH$_2$CH$_2$CH$_2$—), ethylenecarbamoyl (—(O=C)NHCH$_2$CH$_2$—) propylenethiocarbamoyl (—(S=C)NHCH$_2$CH$_2$CH$_2$—), ethyleneoxyacetimidoyl, ethyleneoxyethylenethiocarbamoyl, propyleneoxypropylenecarbamoyl and diethyleneoxy acetimidoyl (—CH$_2$CH$_2$OCH$_2$CH$_2$OCH$_2$(C=NH)—)

Turning now to consideration of individual compounds, the first group of compounds are the alkaloids. Of particular interest among the alkaloids are the opiate alkaloids which will have for the most part the following formula:

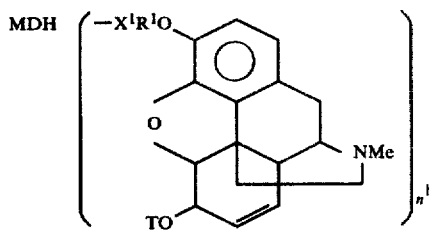

wherein:

T is hydrogen or acetyl, usually hydrogen, $n^1$ is on the average 1 to 14, usually 1 to 12, more usually 2 to 12;

$R^1$ may be the same as R, but will usually be either (1) an aliphatic group, either branched or straight chain, having from 0 to 1 site of aliphatic unsaturation, e.g. ethylenic and of from 1 to 8 carbon atoms, more usually of from 1 to 6 carbon atoms, and preferably of from 1 to 4 carbon atoms and has from 0 to 3, usually 0 to 2 heteroatoms, which are oxygen, sulfur or nitrogen, usually oxygen and nitrogen, and bonded to X with other than sulfur and oxygen, and bonded to oxygen through carbon, wherein the oxygen is present as oxocarbonyl or oxy, particularly ether, and the nitrogen is present as tertiary amino; or (2) aromatic hydrocarbon, e.g. arylene, alkarylene or aralkylene of from 6 to 9 carbon atoms; and $X^1$ is a bond, non-oxocarbonyl (including thio and imino analogs thereof), or diazo, when bonded to an aromatic annular carbon atoms, i.e. when $R^1$ is aromatic hydrocarbon.

Illustrative groups for —$R^1$—$X^1$— include carboxymethyl, imidoylmethyl, thiocarbamoylethyl, diazophenyl, ethylene, ethyleneoxyethylene, carboxymethyleneoxyethyl, 2-(1-carboxypropylene) and N-methyl imidoylmethylaminoethyl.

The next group of compounds are cyclic lactams or urea compounds of the following formula:

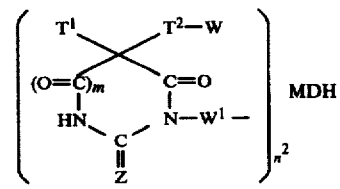

wherein:

$n^2$ is on the average from 1 to 14, usually 1 to 12, more usually of from 2 to 12;

$T^1$ and $T^2$ are hydrocarbon of from 1 to 7 carbon atoms, more usually of from 1 to 6 carbon atoms, and have from 0 to 1 site of aliphatic unsaturation, e.g. ethylenic, including ethyl, n-butyl, α-methylbutyl, isoamyl, allyl, hexyl, $\Delta^1$-cyclohexenyl and phenyl, and when m is 0 phenyl;

one of W and $W^1$ is —$R^2$—$X^2$— and the other is hydrogen;

Z is oxygen, with the proviso that Z may be $H_2$ when one of $T^1$ and $T^2$ is phenyl, e.g. primidone.

m is 0 when the compound is diphenylhydantoin, and 1 when the compound is a barbiturate or Z is $H_2$;

$R^2$ may be the same as R but is usually an aliphatic group of from 1 to 8 carbon atoms, usually of from 1 to 6 carbon atoms, and preferably of from 1 to 4 carbon atoms, and from 0 to 3 heteroatoms, usually of from 0 to 2 heteroatoms, and from 0 to 1 site of aliphatic unsaturation, where the heteroatoms, are oxygen, sulfur and nitrogen, usually oxygen and nitrogen, $R^2$ being bonded to nitrogen through an aliphatically saturated carbon atom and to $X^2$ with other than oxygen and sulfur; or aromatic hydrocarbon of from 6 to 9 carbon atoms; and $X^2$ is a bond, non-oxocarbonyl including the nitrogen and thioanalogs thereof, or diazo when bonded to an aromatic annular carbon atom.

Illustrative groups for —$R^2$—$X^2$— include diazo, methylene, ethylene, butylene, ethyleneoxyethyl, acetyl, imidoylmethyl, propyleneoxyacetimidoyl, carboxyvinylene, carboxypropylene, imidoylbutylene, N-methyl ethyleneaminoethyl, N-methyl ethyleneaminoacetyl, and 1-(1-carboxyethylene).

The next group of compounds are the steroids, which include the estrogens, gestogens, androgens, adrenocortical hormones (glucocorticoids and mineral corticoids and bile acids). Of particular interest are the sex hormones and the adreocortical hormones. The steroids will be divided into two groups depending on whether the A ring is aromatic or cycloaliphatic.

For the most part, those compounds which are gestogens androgens, or adrenocortical hormones will come within the following formula:

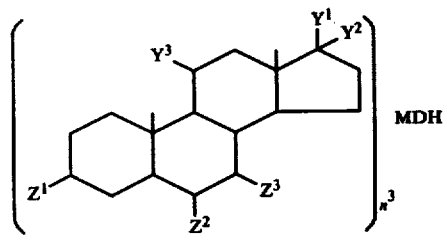

wherein:

one of $Z^1$, $Z^2$, and $Z^3$ is-$R^3$-$X^3$-, wherein the $R^3$ may be singly or doubly bonded to the annular carbon atom. $R^3$ may be the same as R, but is usually an aliphatic group having from 0 to 1 site of aliphatic unsaturation and of from 1 to 8 carbon atoms, usually of from 1 to 6 carbon atoms, and more usually of from 1 to 4 carbon atoms, having from 0 to 3 heteroatoms which are oxygen, nitrogen and sulfur, usually oxygen and nitrogen, $R^3$ being bonded to $X^3$ at other than oxygen and sulfur; or aromatic hydrocarbon of from 6 to 8 carbon atoms;

$X^3$ is a bond, non-oxocarbonyl including the nitrogen and sulfur analogs thereof, or diazo, when bonded to an aromatic annular carbon atom;

when other than —$R^3$—$X^3$—, $Z^2$ and $Z^3$ are hydrogen;

when the compound is a gestogen, there is from 0 to 1 site of ethylenic unsaturation in the $\Delta^4$ or $\Delta^5$ position, and when other than —$R^3$—$X^3$, $X^1$ is hydroxyl or oxo;

$Y^1$ is acetyl; and $Y^2$ and $Y^3$ are hydrogen;

when the compound is an androgen, when other than —$R^3$—$X^3$, $Z^1$ is oxo;

$Y^1$ is hydroxyl; and $Y^2$ and $Y^3$ are hydrogen;

when the compound is an adrenocortical hormone; when other than —$R^3$—$X^3$, $Z^1$ is oxo;

$Y^1$ is hydroxyacetyl;

$Y^2$ is hydrogen or hydorxyl; and $Y^3$ is hydroxy or oxo;

$n^3$ on the average will be in the range of 1 to 14, usually 1 to 12, more usually in the range of 2 to 12.

When the compound is an estrogen and the A ring is aromatic, the compounds will for the most part have the following formula:

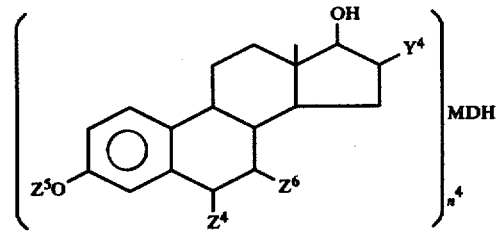

wherein:

one of $Z^4$, $Z^5$, and $Z^6$ is —$R^4$—$X^4$—, wherein when $Z^4$ or $Z^6$ is —$R^4$—$X^4$—, $R^4$ may be singly or doubly bonded to the annular carbon atom, wherein $R^4$ may be the same as R, but is usually an aliphatic radical having from 0 to 1 site of aliphatic unsaturation and of from 1 to 8 carbon atoms, usually of from 1 to 6 carbon atoms, and more usually of from 1 to 4 carbon atoms and from 0 to 3 heteroatoms which are oxygen, nitrogen and sulfur, more usually oxygen and nitrogen, or aromatic hydrocarbon of from 6 to 8 carbon atoms, and $X^4$ is non-oxocarbonyl including the nitrogen and sulfur analogs thereof, or diazo when bonded to an aromatic annular carbon atom;

when other than —$R^4$—$X^4$—, $Z^4$, $Z^5$ and $Z^6$ will be hydrogen;

$Y^4$ is hydrogen or hydroxyl; and $n^4$ on the average is in the range of from 1 to 14, usually 1 to 12, more usually in the range of from 2 to 12.

Illustrative groups for —$R^3$—$X^3$— and —$R^4$—$X^4$— include ethylene, ethyleneoxyacetyl, iminoxyacetyl, p-phenylenediazo, ethylenethiocarbamoyl, carboxybutylene, imidoylpropylene, p-diazobenzyl and thioether-acetyl.

The next compounds are methadone derivatives which will, for the most part, have the following formula:

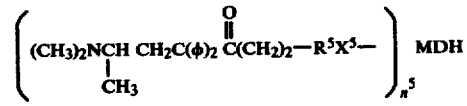

wherein:

$R^5$ may be the same as R, but is usually an aliphatic radical of from 1 to 8 carbon atoms, usually of from 1 to 6 carbon atoms, and more usually of from 1 to 4 carbon atoms; and from 0 to 3 heteroatoms which are oxygen, sulfur and nitrogen, particularly oxygen and nitrogen;

$X^5$ is non-oxocarbonyl including the nitrogen and sulfur analogs thereof; and $n^5$ is on the average in the range of from 1 to 14, usually 1 to 12, more usually in the range of from 2 to 12.

The next group of compounds are associated with steroids and are cardiac glycosides and aglycones of which digoxigenin and digoxin are well known members. For the most part, the compounds will have the following formula:

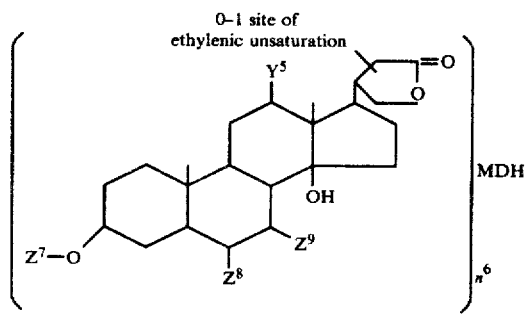

wherein:

one of $Z^7$, $Z^8$, and $Z^9$ is $-R^6X^6-$, wherein when $Z^8$ and $Z^9$ are $R^6$, $R^6$ may be singly or doubly bonded to the annular carbon atom, wherein $R^6$ may be the same as R, but is usually an aliphatic radical having from 0 to 1 site of aliphatic unsaturation and of from 1 to 8 carbon atoms, usually of from 1 to 6 carbon atoms, and more usually of from 1 to 4 carbon atoms and from 0 to 3 heteroatoms, usually of from 0 to 2 heteroatoms, which are oxygen, sulfur or nitrogen, preferably oxygen and nitrogen, or aromatic hydrocarbon of from 6 to 9 carbon atoms, or a mono- or disaccharide residue modified by splitting a glycol group to a dialdehyde and condensing the dialdehyde to an amine or modifying the sugar to provide a uronic acid, the sugars being the naturally present glycosidic groups, and $X^6$ is non-oxocarbonyl including the nitrogen and sulfur analogs thereof, a bond, or diazo when bonded to an annual aromatic carbon atom.

When other than $-R^6-X^6-$, $Z^7$, $Z^8$ and $Z^9$ are hydrogen;

$Y^5$ is hydrogen or hydroxyl; and $n^6$ is on the average in the range of from 1 to 14, usually 1 to 12, more usually in the range of from 2 to 12.

The same groups illustrative of $-R^3-X^3-$ are also illustrative of $-R^6-X^6-$.

The next group of compounds are the cannabinoids. These compounds when conjugated to malate dehydrogenase have for the most part the following formula:

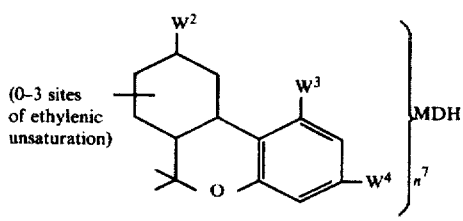

wherein:

any one of $W^2$, $W^3$ or $W^4$ is $R^7-X^7$, wherein when $W^2$ is $R^7$, $W^2$ may be singly or doubly bounded to an annular carbon atom; $W^{2-4}$ may be the same as R, usually being an aliphatic group having a total number of atoms other than hydrogen of from 2 to 8, more usually from 2 to 6 atoms, including from 0 to 2 heteroatoms of atomic number 7 to 8 (oxygen and nitrogen), either in the chain or bonded to the chain, and having from 0 to 1 site of ethylenic unsaturation as the only unsaturation; and $X^7$ may be the same as X, more usually being a bond or non-oxocarbonyl, including the nitrogen and sulfur analogs thereof;

when other than $R^7-X^7-$, $W^2$ is methyl, hydroxymethyl or carboxyl, $W^3$ is hydroxyl or methoxyl, and $W^4$ is pentyl or hydroxypentyl;

$n^7$ is on the average in the range of from 1 to 14, usually 1 to 12, more usually in the range of about 2 to 12.

The unsaturation in the cyclohexane ring is usually delta-8 or -9, or the ring is saturated or aromatic.

Illustrative groups for $R^7-X^7$ include O-carboxymethyl forminoxy, O-carboxyethyl iminoxyl, N-carboxybutyl formamidyl, and carboxypropoxy.

Among aminoacids of interest are the polyiodothyronines. For the most part, the polyiodothyronines have from 3 to 4 iodo groups in the 3, 3', 5, 5'-positions. These compounds will have the following formula:

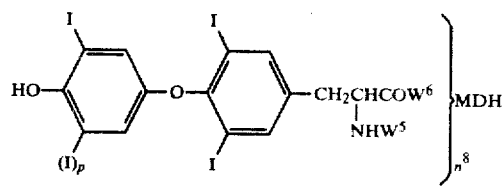

wherein:

one of $W^5$ and $W^6$ is $R^8$-$X^8$; $R^8$ may be the same as R, but is usually an aliphatic group of from 2 to 10, more usually from 2 to 8 carbon atoms, having from 0 to 4, more usually 0 to 2 heteroatoms, which are of atomic number 7 to 8 (nitrogen and oxygen), which are present as oxy, nonoxocarbonyl, amido or tert.-amino, there being from 0 to 1 site of aliphatic saturation, normally ethylenic;

$X^8$ is a bond or nonoxocarbonyl, including the nitrogen and sulfur analogs thereof;

when other than $-R^8-X^8-$, $W^5$ is hydrogen; and $W^6$ is hydroxyl, alkoxy of from 1 to 3 carbon atoms or amino;

p is 0 or 1; and $n^8$ is on the average in the range of from 1 to 14, usually 1 to 12, more usually in the range of 2 to 12.

Illustrative groups for $-R^8-X^8$ include succindioyl, glutardioyl, diglycolicdioyl, acetyl, propinyl, butylene, and N-methyl 3-azaglutardioyl.

Numerous other compounds may be conjugated to malate dehydrogenase employing the same types of sites for linking to the ligand and the same types of linking groups as exemplified above.

In preparing the conjugates, it is desirable that at least 2, preferably at least 10 and particularly preferred at least 40% of the original enzyme activity is retained. Furthermore, the enzyme is substituted in such a manner so that when one or more groups are bonded to the enzyme, and are bound by antibody, the activity of the enzyme is reduced by at least 30% of its original activity after conjugation, usually at least 40%, and preferably by at least 50%.

Various ways can be employed for conjugating the various compounds or ligands to the malate dehydrogenase. The conditions employed will normally reflect the particular functionality which is employed in forming a bond to the malate dehydrogenase. The functionalities which find primary use are the mixed anhydride employing an alkyl chloroformate, acyl azide, the imidate ester, thioimidate, isothiocyanate or reductive alkylation with an aldehyde. Normally, the groups will be bonded to available amino groups of lysine as the major mode of conjugation, and therefore amides, amidines, ureas, thioureas, and alkylamines will be formed.

The reaction mixture will normally be buffered to a pH in the range of 5 to 10, more usually in the range of 6 to 9. Various buffers may be used, such as phosphate, carbonate, Tris, and the like. An aqueous solvent will normally be used, and a preferred solvent includes from about 10 to 40 weight percent of an oxyethylene alcohol or ether having from 1 to 3 oxyethylene units. Particularly useful is carbitol. The temperatures will normally be at or above −5° C. and generally less than about 40° C., usually from about 0° to 25° C.

The concentration of the enzyme will vary widely, generally ranging from about 0.05 to 5, more usually from about 0.1 to 1 mg/ml. The amount of ligand to be conjugated will vary, depending on the ligand enzyme ratio which is desired.

EXPERIMENTAL

The following examples are offered by way of illustration and not by way of limitation.

All temperatures not otherwise indicated are in centigrade. All percents not otherwise indicated are by weight.

EXAMPLE I $O^3$-carboxymethyl morphine conjugate to malate dehydrogenase

A. Porcine heart malate dehydrogenase (MDH) (0.3 cc., $1 \times 10^{-7}$ moles MDH) as a 10 mg./ml. suspension in 3.2 M ammonium sulfate, was centrifuged. The pellet was dissolved in 0.2 cc. of water and dialyzed against 125 cc. of water at 3° for 3.5 hours with one water change. The dialysate was diluted to 1 cc. with a solution 0.15 M sodium phosphate and 0.075 M sodium carbonate at pH 9.0. Seventy-four μl. of the mixed anhydride solution prepared as described below was added in 5 μl. increments with stirring at 0°. During the addition, the pH was maintained between 8.8 and 9.0. After the addition was complete, the solution was adjusted to pH 9.5 and stirred for 1.5 hours at room temperature. The solution was dialyzed for 24 hours against 125 ml. of 0.05 M phosphate-0.05 M carbonate buffer, pH 9.3 at 3° with three buffer changes. The malate dehydrogenase was found to have about 27 morphine groups per enzyme molecule.

B. To a suspension of $O^3$-carboxymethyl morphine (514 mg., 1.5 mmoles) in 15 ml anh DMF was slowly added 196 μl (1.5 mmoles) of isobutylchloroformate at −5° and the mixture stirred at the same temperature for sixty minutes to provide a 0.1 M solution of the mixed anhydride.

EXAMPLE II $O^3$-carboxymethyl morphine conjugate to malate dehydrogenase

The following was a study concerning the effect of increasing substitution by carboxymethylmorphine with porcine heart malate dehydrogenase.

Malate dehydrogenase (4.0 ml., 40.0 mg., Calbiochem Lot 101089) was centrifuged (17,500 r.p.m., 20 minutes). The resulting pellet was dissolved in 1 ml. of distilled water and dialyzed against 250 ml. of 0.01 M phosphate buffer, pH 7.5 at 3° with $2 \times 250$ ml., buffer changes in 4 hours. The resulting dialysate was diluted to 5 ml. with 0.15 M phosphate-0.075 M carbonate, pH 9.0, to give a solution approximately 0.1 M phosphate-0.05 M carbonate. The solution was divided into two 2.5 ml. portions.

One of the portions was cooled to approximately 0° in an ice bath, and a 0.1 M solution of radioactive $O^3$-carboxymethylmorphine isobutyl carbonate mixed anhydride ($2.43 \times 10^5$ counts per minute per μmole) was added with rapid stirring in 4–5 μl. increments. Four aliquots of from 0.4–0.5 ml. were withdrawn at apprpriate times, the additions and withdrawals being carried out at the following schedule, while maintaining the pH of the solution between 8.8 and 9.0. The samples were withdrawn when the pH indicated reaction had occurred.

The total additions prior to each sample withdrawal were; (1) 15 μl.; (2) 25 μl.; (3) 19.8 μl.; (4) 34 μl.; (5) 41.5 μl. Five minutes after the last aliquot was added, the sample was withdrawn.

The pipettes employed to withdraw the 0.5 ml. samples were each rinsed with 0.25 ml. 0.05 M phosphate-0.05 M carbonate buffer, pH 9.5. The original solutions and rinses were quantitatively transferred to dialysis sacks with proper rinsing and dialyzed for about 48 hours at 3° against the same phosphate-carbonate buffer with $5 \times 250$ ml. buffer changes.

The samples were then quantitatively removed from the dialysis bags, using the same buffer rinses and diluted to 2 ml. with the same buffer. Sample number four had a small amount of precipitate, while sample number five had a large amount of precipitate. Both samples were centriguged, (17,500 r.p.m., 20 minutes). The pellet from sample four was washed with buffer, twice with small amounts of water, followed by an alcohol wash, and then dried in a nitrogen stream, a yield 0.2 mg. Efforts to dissolve the precipitate from sample number five were not satisfactory.

From each of the samples, a 0.5 ml. aliquot was withdrawn, (the supernatant of sample four was employed) and each added to 10 ml. of scintillation fluid and counted. Sample number one had a count of 11,350; sample number two 33,700, sample number three 55,200; and sample number four 80,100.

This calculates out to 3.4, 10.4, 17.3, and 27.8 morphine molecules per enzyme for the first to fourth samples. Because of the substantial insolubility of the fifth sample, no data were obtained for it.

The second sample of enzyme was treated substantially in the same manner as described above to give an additional four samples of carboxymethylmorphine substituted malate dehydrogenase, labeled with 3.2, 6.1, 13.2, and 17.3 morphine.

The samples were then assayed as follows: an assay solution was prepared by combining 0.92 ml. of 0.5 M phosphate buffer, 50 μl. of 7 mM. oxaloacetate in phosphate buffer, 20 μl. of 14 mM, NADH and 1 μl. of $3.67 \times 10^{-5}$ in binding sites of antibody (binding sites determined by FRAT ®, an ESR technique supplied by Syva Co.) which is a large excess over the morphine present. To this solution was added 10–20 μl. of the carboxymethylmorphine modified malate dehydrogenase, which had been diluted 1,000 fold with 1 M potassium monoacid phosphate solution.

The rate of the reaction can be followed by metering the change in optical density, at 340 nm. Approximately 30 seconds is required to mix the various reagents and the reading is then taken for the second or the third minute, depending on which gave the faster rate. Since thermodynamic equilibrium is not achieved within the time the readings are taken, the rate is changing with time. However, by repeating the same procedure before and after the addition of antibody, relative percents inhibition can be obtained for the time limit which is desirable for a commercial assay.

| Sample number | Activity without Ab, OD/min. | Activity with Ab, OD/min. | Percent inhibition |
|---|---|---|---|
| 1a | 0.117 | 0.087 | 26 |
| b | 0.141 | 0.116 | 18 |
| 2a | 0.078 | 0.039, 0.037 | 53 |
| b | 0.125 | 0.087 | 30 |
| 3a | 0.071 | 0.017, 0.015 | 78 |
| b | 0.125 | 0.048 | 62 |
| 4a | 0.066 | 0.008, 0.009 | 86 |
| b | 0.143 | 0.033 | 77 |

The above data demonstrate two facts for malate dehydrogenase: (1) with increasing substitution there is decreasing initial activity; and (2) with increasing substitution there is increased inhibitability for the enzyme. Therefore, when randomly substituting malate dehydrogenase, one compromises between the percent inhibition to obtain an acceptable assay and initial activity of the enzyme.

EXAMPLE III p-Diazobenzamide modified insulin conjugate to malate dehydrogenase A. To a suspension of 4.1 g. (30 mmoles) of p-aminobenzoic acid in 300 cc. of water was added 4.5 cc. of concentrated hydrochloric acid. The suspension was warmed slightly to hasten solution, at which time an addition of 9 cc. of concentrated hydrochloric acid was added and the solution cooled to 0°–5°. To this stirring solution was added at once a precooled solution of 2.1 g. of sodium nitrite in 6 cc. of water. After 15 minutes at 0° a test with starch iodide paper indicated excess nitrous acid. The pH was raised to the pH range of congo red by the addition of saturated aqueous sodium acetate. To this solution was added at once 6.3 g. of sodium sulfite in 15 cc. of water. A certain amount of color was produced at this step and some precipitation was observed as well. The solution could be assayed for active diazonium salt or the reactive syn isomer, (1) by touching a drop to filter paper which had been treated with β-naphthol in aqueous alcoholic carbonate solution. An instantaneous red color signaled the presence of the reactive species. After one hour at room temperature, this spot test showed no active dizonium species remaining. The aqueous solution was treated with decolorizing charcoal and filtered. The addition of solid sodium chloride to saturation caused the precipitation of the desired anti-diazosulfonate as a yellow crystalline solid which is shown by spectroscopic techniques to be the monhydrate.

B. To 500 mg. of disodio para-(anti-diazosulfonato) benzonate ($1.7 \times 10^{-3}$ moles) and 10 ml. of dry dimethyl formamide (DMF) cooled in an ice bath to 0° was added one ml. of isobutyl chloroformate ($7.61 \times 10^{-1}$ moles) followed by 1.5 ml. of triethylamine. The mixture was stirred for three hours at 0° followed by standing for 2 days in a cold room with stirring. Excess chloroformate and dimethylformamide were removed by rotary evaporation at 40°.

C. The supernatant resulting from slurrying 30 mg. of insulin with pH 8.8 tris-barbital buffer was combined with 50λ ($6.85 \times 10^{-3}$ mmoles) of the anhydride prepared above. The mixture was stirred for 2.5 hours at 4°, at the end of which time, the solution was dialyzed against pH 8.8 tris-barbital buffer.

The above solution was then combined with 0.25 ml. (10 mg./ml, $3.4 \times 10^{-5}$ mmoles) of dialyzed malate dehydrogenase (dialyzed against tris-barbital buffer, pH 8.8) and the solution irradiated with visible light (greater than 398 nm.) for approximately 45 minutes. A small sample was combined with β-naphthol, the solution turning red, indicating that all the diazosulfonate had not reacted.

The resulting product was chromatographed through a column of Sephadex G-50 swelled with bicarbonate pH 8.8 buffer. Five λ of the solution had an activity when assayed for malate dehydrogenase of about 0.12 OD/min.

EXAMPLE IV

Testosterone-3-carboxymethyloxime conjugate to malate dehydrogenase

The testosterone-3-carboxymethyloxime, 36.1 mg. (100 μmole), was dissolved in 1 ml. of dimethylformamide containing 3 drops of triethylamine. The solution was cooled to −15° and 13.1 μl. (100 μmole) of isobutylchloroformate was added. Stirred for 1 hour at −15° to −5° during which time the solution turned light orange.

Malate dehydrogenase, 0.5 cc. of 10 mg./ml. suspension in 2.8 M ammonium sulfate (5 mg. MDH, $6.8 \times 10^{-6}$ mole MDH, $44 \times 10^{-6}$ mole MDH, $44 \times 10^{-6}$ mole lysine residue) was centrifuged at 15,000 r.p.m. for 20 min. The pellet was dissolved in 1 ml. of water and the solution was dialyzed against water at 4° for 5 hours (3 changes). The solution was brought to pH 8.5 with dilute NaOH at 4° and 44 μl. of the mixed anhydride solution (4.4 mmole mixed anhydride; corresponds to 1 hapten per lysine) was added to the stirred enzyme solution in three portions over 5 minutes. Sodium hydroxide solution was added as needed to keep the pH at 8.5. Initially the solution was turbid, but cleared during 1 hour stirring at 4°.

The solution was exhaustively dialyzed against 0.05 M phosphate buffer, pH 7.5. A small amount of sediment was removed by centrifugation.

Assay

Because of the instability of highly diluted enzyme solutions, the stock solution (5 mg./ml.; $3.4 \times 10^{-5}$ M) was diluted 1 to 500 just prior to each assay. The order of addition of reagents to the assay mixture was as follows: (1) antibody (when used), (2) diluted enzyme, (3) oxaloacetic acid, (4) NADH. The final enzyme concentration was $2.7 \times 10^{-9}$ M. The antibody concentration was not known. Sufficient antibody was used to achieve greater than 40% inhibition of the enzyme activity. This corresponded to an equivalent of 10 μl. of antibody containing serum.

(1) Enzyme Alone—0.073 OD/min. (2) Enzyme+Antibody—0.042 OD/min. (3) Enzyme+Antibody+50 μl. $10^{-5}$ M testosterone (added first)—0.073 OD/min.

EXAMPLE V

3-(O-carboxymethyl) estradiol conjugate to malate dehydrogenase

To 33.0 mg. ($10^{-4}$ mole) of 3-(O-carboxymethyl) estradiol dissolved in 1 ml. of anhydrous dimethylformamide was added 2 drops of triethylamine. The solution was cooled to $-15°$, and 13.1 µl. ($10^{-4}$ mole) of isobutylchloroformate was added. The solution was maintained at $-15°$ for 1 hour.

The above solution (44 µl.) was added to a solution of 5 mg. malate dehydrogenase in 0.004 M $Na_2HPO_4$, pH 9 which had been cooled to 4°. During the reaction the pH was maintained at 8.5 to 9.0 by adding sodium hydroxide solution. The solution, turbid initially, cleared after 2 hours. It was dialyzed exhaustively against 0.05 M sodium phosphate, pH 7.5; then clarified by centrifugation.

Assay

The stock enzyme solution was diluted 1 to 1000 with 1 M $Na_2HPO_4$ solution and assayed in the customary manner entailing following the oxidation of NADH in the presence of oxaloacetic acid at 340 nm., 30°. Antiestradiol antibodies were prepared in rabbits and the γ-globulin ($4 \times 10^7$ M binding sites) fraction was used in this assay.

(1) 20 µl. of the enzyme solution has an activity of 0.107 OD/min.

(2) Addition of 5 µl. of the antibody solution reduced the activity to 0.070 OD/min.

(3) Addition of (a) 5 µl. of antibody, and (b) 20 µl. of the enzyme to the assay mixture containing 20 µl. of $10^{-3}$ M estradiol gave 0.106 OD/min.

EXAMPLE VI

Conjugation of $\Delta^8$-aldehydetetrahydrocannabinol carboxymethoxime to MDH (A) To 2.86 mg (7.13 µmole) of $^{14}$C-$\Delta^8$-9-aldehyde tetrahydrocannabinol carboxymethoxime was added, at 0°, 125 µl of a stock solution of a reagent prepared by mixing ECDI (ethyl dimethylamminopropyl diimide)) (15.7 mg, 81.8 µmole), N-hydroxysuccinimide (8.2 mg, 71.3 µmole) and triethylamine (9.9 µl, 71.1 µmole) in 1 ml of N, N-dimethylformamide under nitrogen at 0°. The resulting activated ester (0.057 µmole)/µl) was then stirred at 5° overnight.

(B) To MDH (4 mg, 0.057 µmole) in 2.24 ml of carbonate buffer was added 0.45 ml of cold (5°) DMF slowly with constant stirring at 0°-5°. To the resulting enzyme (13.5% deactivated) was added aliquots of the above prepared ester (4 µl, 4 haptens/enzyme). After the addition of 16 haptens/enzyme, the enzyme (92% deactivated) solution became slightly cloudy and was centrifuged at 10 K rpm for 15 minutes. The supernatant was first dialyzed against $3 \times 500$ ml carbonate buffer (pH 9, 0.05 M) and then $2 \times 500$ ml phosphate buffer (1 M, pH 9.0). The resulting conjugate was 61% deactivated after clean up (hapten number 14).

EXAMPLE VII

Conjugation of $^{14}$C-11-nor-9-keto-$\Delta^{11}$-tetrahydrocannabinol carboxymethoxime to MDH (A) To $^{14}$C-11-nor-9-keto-$\Delta^{11}$-tetrahydrocannabinol carboxymethoxime, (1.11 mg., 2.85 µmole) was added 56 µl of mixture of ECDI and N-hydroxysuccinimide prepared by stirring ECDI (25 mg, 130 µmole), N-hydroxysuccinimide (13 mg, 115 µmole) and triethylamine (16.0 µl, 115 µmole) in N,N-dimethylformamide (2 ml, dried over molecular sieves 3A) at 5° under nitrogen. The resulting NHS ester (0.0509 µmole/µl) was allowed to stand in the cold room overnight.

(B) To MDH (pig heart mitochondrial) 3.56 mg, 0.0509 µmole) in 2 ml of carbonate buffer (0.05 M, pH 9) was added slowly 450 µl of cold N,N-dimethylformamide (18% cosolvent) using a repeating dispenser at 0°-5°. To the resulting enzyme solution was added aliquots of THC-activated ester (1 µl per hapten/enzyme). After the addition of 10 haptens/enzyme, the enzyme was 95% deactivated. It was then dialyzed against $3 \times 250$ ml carbonate buffer (pH 9, 0.05 M) and then $2 \times 250$ ml 1 M $KH_2PO_4$ (pH 9). The resulting conjugate (65% deactivated after clean up, hapten number 6.7) showed 64% inhibition with excess anti(O-carboxymethyl $\Delta^8$-tetrahydrocannabinol conjugate to bovine serum albumin).

EXAMPLE VIII

Conjugation of O-carboxymethyl-$\Delta^8$-THC to MDH through NHS intermediate (A) To $^{14}$C-O-carboxymethyl $\Delta^8$-THC (2.34 mg, 6.29 µmole) was added, at 0°, 100 µl of a mixture of ECDI and N-hydroxysuccinimide (NHS) prepared by stirring ECDI (25 mg, 130 µmoles), N-hydroxysuccinimide (13.2 mg, 114 µmoles) and triethylamine (15.8 µl, 114 µmoles) in N,N-dimethylformamide (2 ml, dried over molecular sieves 3A) under nitrogen at 0°. The resulting activated ester was stirred at 5° overnight.

(B) To MDH (4 mg, 0.057 µmole) in carbonate buffer (ph 9, 0.05 M, 800 µl) was added 180 µl of cold DMF at 0° using a repeating dispenser over a period of 12 minutes. To the resulting enzyme (13% deactivated) was added portions of NHS ester (0.057 µmole/µl). After the addition of 10 haptens/enzyme, the enzyme (98% deactivated) was dialyzed against $4 \times 250$ ml of carbonate buffer (0.05 M, pH 9), $1 \times 250$ ml of 1 M $K_2HPO_4$ (pH 9), and followed by one pass through Sephadex gel (G15, 1 M $K_2HPO_4$, pH 9, 13% yield). The purified enzyme was 96% deactivated, having a hapten number of 8, and showed inhibition of 46% with excess anti(O-carboxymethyl $\Delta^8$-tetrahydrocannabinol conjugate to bovine serum albumin).

EXAMPLE IX

Conjugation of $^{14}$c-glycyl cannabinolic acid to malate dehydrogenase (MDH)

(A) Preparation of NHS ester: To $^{14}$C-glycyl cannabinolic acid amide (2.75 mg, 6.9 µmole) (GCA) was added 50 µl of the mixture of a reagent which was prepared by stirring ECDI (15.4 mg, 80 µmole), N-hydroxysuccinimide (8.1 mg, 70 µmole) and triethylamine (10 µl, 71 µmole) in N,N-dimethylformamide (500 µl, dried over molecular sieves 3A) at 0° under nitrogen. The GCA-activated ester (0.138 µmole/µl) was then stirred overnight in cold room .

(B) To MDH (9.8 mg, 0.140 µmole) in carbonate buffer (2.0 ml, 0.05 M, pH 9.2) was added slowly cold, N,N-dimethyl formamide (450 µl, 18%) using a repeating dispenser over a period of 40 minutes. The enzyme was 2.7% deactivated after addition of DMF. The 2-5 µl of GCA activated ester was added slowly with constant stirring. The enzyme conjugate was 55% deactivated after addition of fifteen haptens (reaction time 3 hours). Half of the total reaction mixture (1.1 ml) was withdrawn and centrifuged (10K rpm) at 0° for 15 minutes. The supernatant was dialyzed against 1×250 ml carbonate buffer (ph 9, 0.05 M). Another forty-four haptens (a total of 59 fold hapten/enzyme, reaction time 4½ hrs) was added to the rest of the enzyme mixture. The enzyme (85% deactivated) solution was centrifuged (10K rpm) at 0° for 15 minutes and the supernatant was dialyzed against 1×250 ml carbonate buffer (0.05 M, pH 9). Both enzyme conjugates were passed through Sephadex G-50 twice. The properties of the two conjugates are (1) 85% deactivated, hapten number 11.8 and (2) 55% deactivated, hapten number 1.6. The conjugate (1) was 45% inhibited by antibodies to the conjugate of carboxymethyl cannabinol to bovine serum albumin of which about 20% was recoverable by the addition of cannabinolic acid and glycyl cannabinolic acid.

EXAMPLE X

Conjugations of
$^{14}$c-11-nor-9-keto-$\Delta^{11}$-tetrahydrocannabinol
carboxymethoxime to MDH via the
N-hydroxysuccinimide ester (A) A benzene solution of the name compound (0.89 ml, 9.0 mM) was evaporated in vacuo in a 5 ml pear-shaped flask to give 3.1 mg of an orange syrup. A 40 μl portion of a 1.0 ml anhydrous dimethylformamide solution of 25.3 mg (0.22 mmoles) N-hydroxysuccinimide and of 38.4 mg (0.20 mmoles) ECDI was added to the 3.1 mg (8.0 μmoles) of the name compound (Sp.act=2.27×10$^8$ cpm/mmole) contained in the flask chilled to 0°. The resulting pale yellow solution was stored for 4 days under argon at 0°.

(B) A stock solution of porcine mitochondrial MDH (3.00 ml, Miles, Lot. No. R20A) was prepared from an ammonium sulfate suspension. The protein was collected by centrifugation at 17,500 rpm for 20 min at 0°. The supernatant which contained a small amount of flocculent solid was decanted with a dropper leaving a white pellet with an orange spot at the bottom. The pellet was dissolved in 1.50 ml of water, and the insoluble orange contaminating material removed by centrifugation at 17,500 rpm for 20 min at 0°. The supernatant was decanted with a dropper, and the orange pellet washed gently with 2–0.6 ml portions of 0.01 M sodium carbonate, pH 9.0. The supernatant and washes were quantitatively transferred to a dialysis sac and dialyzed against 5×125 ml portions 0.05 M sodium carbonate, pH 9.0 over a four day period at 0°. After dialysis the clear solution was quantitatively transferred using 2×0.2 ml buffer washes and made up to 5.60 ml containing 5.09 mg/ml protein. (Enzyme activity indicated 95% recovery of MDH from (NH$_4$)$_2$SO$_4$ suspension.)

(C) Sodium carbonate, 0.200 ml, 0.05 M, pH 9.0; dipotassium hydrogen phosphate, 0.050 ml, 4.0 M; and 0.160 ml H$_2$O were added to 0.80 ml of stock enzyme with stirring at 0°. The pH of the solution was adjusted to 9.0 with 3 μl of 1.0 M HCl with rapid stirring. Aliquots, 0.5 μl, of the dimethylformamide solution of N-hydroxysuccinimide ester of the named compound were added with rapid stirring at 0° at one minute intervals until the desired amount was added (0.5–9.0 μl). Aliquots, 5 μl, of the reaction solution were withdrawn between additions of N-hydroxysuccinimide ester. These were used to monitor the course of the reaction by assaying for enzyme activity. Often during the addition, white insoluble specks would appear in the reaction solution (probably insoluble ester) which gradually dissolved with continued stirring. However, some of the conjugations became turbid, especially those where larger amounts of reagent were added, and these solutions did not clear upon continued stirring. The pH changed to slightly lower values during reagent addition, 0–0.1 pH unit. The solution was stirred overnight at 0°, then quantitatively transferred to a dialysis sac with 2×0.1 ml dialysis buffer rinses. It was dialyzed for 5 days against 5×125 ml portions of 0.10 M sodium phosphate—20% carbitol buffer, pH 7.7 then for 2 days against 3–125 ml portions of 0.10 M sodium phosphate buffer, pH 7.4 to remove the carbitol.

After dialysis, the conjugate was transferred quantitatively using 2×0.2 ml dialysis buffer rinses and made up to 4.00 ml with dialysis buffer. A portion, 0.20 ml, was counted for radioactivity to determine the number of covalently bound THC residues. Another portion, 10 μl, was tested for enzyme activity and inhibition of activity by THC antibody. The following table indicates the results.

TABLE

| Conjugate | Amount NHS Ester per Enzyme | Yield[1] | Average Number THC Residues per Enzyme | Relative Enzyme Activity[2] | % Inhibition with Sheep γ-Globulin |
|---|---|---|---|---|---|
|  | 0.0 | — | 0.0 | 1.0 | 0 |
| A | 1.9 | 34[4] | 0.64 | 0.76 | 14 |
| B | 1.9 | ~49 | 0.95 | 0.71 | 18 |
| C | 3.8 | 61 | 2.3 | 0.58 | 33 |
| D | 5.8 | 53 | 3.1 | 0.34 | 45 |
| D' | 5.3 | 79[5] | 4.2 | 0.29 | 51 |
| E | 8.0 | 65 | 5.2 | 0.19 | 46 |
| F | 9.1 | 59 | 5.4 | 0.18 | 44 |
| G | 19.1 | 64 | 12.2 | 0.08 | 35 |

[1](Moles of THC residues incorporated/moles of NHS ester added × 100
[2]Enzyme assays were performed by diluting concentrates (usually 1:40) into 1.0 M K$_2$HPO$_4$ containing 0.1% RSA at 0° then assaying 5 or 10 μl portions of diluted conjugate in 1.0 ml assays containing 4 mM NAD, 100 mM sodium malate in 0.10 M glycine-0.01% RSA-0.01% EDTA buffer, pH 9.5 at 30°.
[3]Percent reduction of enzyme activity in presence of excess (10 μl) sheep anti-THC γ-globulin.
[4]Lower purity of NHS ester probably accounts for low yield of this conjugate.
[5]Affinity chromatographed with a C$^8$-AMP-sepharose column

EXAMPLE XI

Triiodothyronine conjugate to MDH

A. Triiodothyronine (T$_3$, 1.0 g) was added to 50 ml of dry methanol in a foil wrapped 100 ml round bottom flask which was equipped with a magnetic stir bar and a CaCl$_2$ drying tube. The resulting suspension was cooled in an ice-water bath for one half hour. The flask was maintained in the bath while HCl gas was rapidly bubbled into the reaction mixture for 5 minutes. The reaction mixture was then maintained at room temperature overnight. Slow magnetic stirring was continued through the night. The solvent was removed with a Buchi Rotovapor. After further drying under high vacuum there was obtained 0.914 g of a white powder. Another preparation of the methyl ester (similar conditions) gave a yellowish powder. The colored impurities apparently do not interfere with subsequent reactions as this material when taken through the synthetic scheme and conjugated to MDH gave 50% inhibitable conjugates with MDH (pig heart).

B. The reaction was carried out in a 25 ml round bottom flask wrapped in foil, equipped for magnetic stirring and placed under an Argon atmosphere. A solution of 0.591 g $T_3$-methyl ester hydrochloride was formed in a solvent system consisting of 2 ml DMF mixed with 2 ml THF. To this solution was added 146 $\mu l$ of triethylamine (1.25 equivalents) and the solution was stirred for fifteen minutes. Then 0.130 g (120 equivalents) of N-methyliminodiacetic acid anhydride was added in a single portion. TLC on $SiO_2$ showed complete reaction. The solvent system for TLC analysis was AcOH/MeOH/CHCl$_3$: 5:10:85. The solvent was removed on a Buchi rotoevaporator initially using a water aspirator and finally a mechanical vacuum pump. The water bath temperature was not allowed to exceed 30°. The residue was dissolved in 8.5 ml dry THF. To the solution was added 76 ml of ethyl acetate and the mixture was vigorously shaken. The resulting suspension was gravity filtered and the filtrate was washed in a separatory funnel with 10 ml water, then 20 ml water, then 2×15 ml of a saturated salt solution to dry the solution. Further drying was effected with $MgSO_4$ which was then removed by gravity filtration. The solvent was removed on the evaporator and the product residue was suspended in $CHCl_3$. Petroleum ether was then added as cosolvent in the suspension. The solvent was then removed by filtration and the solid product was dried in a desiccator under vacuum. After drying in the desiccator, 0.346 g of a white powder was obtained.

C. A solution of 8.44 mg (10.6 $\mu$mol) of the product from B (T$_3$-MEMIDA) in 300 $\mu$l of dry THF was prepared in a 5 ml pear shaped flask wrapped in foil and equipped for magnetic stirring. Using 1 ml volumetric flasks a solution of 26.6 mg NHS (0.231 M) in 1 ml THF and a solution of 46.0 mg dicyclohexyl carbodiimide (DCC, 0.223 M) in 1 ml THF were prepared. To the reaction flask containing the T$_3$-MEMIDA was added 48 $\mu$l (11.1 $\mu$mol) of the NHS solution. The reaction mixture was then cooled by placing the reaction flask in an ice-water bath for 20 minutes. To the cooled mixture was added 50 $\mu$l (11.1 $\mu$mol) of the DCC solution. The reaction mixture was kept at ice bath temperature for one hour and then brought to room temperature and left overnight. Large crystals of dicyclohexylurea were present in the reaction flask. The solution was filtered through a glass wool plug in a capillary pipet to remove the urea. The solvent was then removed by Buchi rotoevaporator. The material in the flask was taken up in 0.2 ml of a 20% n-hexane/$CH_2Cl_2$ solution and chromatographed on a cellulose column with 20% n-hexane/$CH_2Cl_2$ as the eluent. The column was prepared in a 5¾ inch length capillary pipet. The size of the fractions was approximately 0.5 ml and the fractions were analyzed by TLC on cellulose. Ester containing fractions were combined and the solvent was removed on a Buchi rotoevaporator. The NHS ester was dissolved in 250 $\mu$l of diglyme. The diglyme solution (5 $\mu$l) was dissolved in 1 ml of 0.1 N NaOH and the uv spectrum of the solution was obtained. The absorbance at 312 nm was used to estimate the concentration of the NHS ester. The value of $4.2 \times 10^3$ was used as the extinction coefficient. The yield was 60.2%.

D. A 2.7 ml aliquot of a 9.61 mg/ml MDH (from pig heart) solution in 50 mM $NaHCO_3$-$Na_2CO_3$ buffer (pH 9.04) was added to a 5 ml Pierce Reacti-vial which was equipped for magnetic stirring and maintained in an ice-water bath. Using a 250 $\mu$l Hamilton syringe, 0.9 ml of carbitol was added to the enzyme preparation at a rate of 25 $\mu$l/minute. Fairly vigorous magnetic stirring was maintained during the addition of the carbitol and later during the addition of the hapten solutions. In a single portion, 63 $\mu$l of a diglyme solution containing the purified NHS ester of $T_3$-MEMIDA ($2.16 \times 10^{-2}$ M) was added by syringe. Twenty minutes was allowed for completion of the reaction. The reaction mixture was then assayed to determine the extent of inactivation of the enzyme and the magnitude of the inhibition by anti-T$_3$. An aliquot of the reaction mixture (1.2 ml) was removed and dialysed against 0.5 M $KH_2PO_4$ (pH 7.0). The NHS ester solution (6 $\mu$l) was added with microcaps. Again 20 minutes were allowed for the reaction to go to completion before assaying. Again, 1.2 ml of the reaction mixture was removed and dialyzed against 0.50 M $KH_2PO_4$ (pH 7.0). Finally 2 $\mu$l of the hapten solution was added to the remainder of the reaction mixture in the Reacti-vial. After 20 minutes the mixture was then dialyzed against 0.50 M $KH_2PO_4$ (pH 7.0).

E. Sephadex G-50 was prepared by overnight swelling in 0.50 M $KH_2PO_4$ (pH 7.0) at 2°–4°. A 0.9×100 cm column of this material was prepared and conditioned by a continuous flow of 0.50 M $KH_2PO_4$ (pH 7.0) for 2 hours and then passage of BSA in an aqueous solution through the column. After 2 days of dialysis against 0.50 M $KH_2PO_4$ (pH 7.0), the conjugates were passed through the column. Fractions were collected. The appropriate fractions were pooled and concentrated at 2° in a collodion bag apparatus. Finally the volume was brought to 1.0 ml with 0.50 M $KH_2PO_4$ (pH 7.0). All of the above steps were carried out in the cold room at 2°–4°. The percent of the original activiity of the enzyme was 54.5 and 47.3, and the percent inhibition was 50.1 and 44.2 respectively.

EXAMPLE XII

Preparation of carboxymethyloxime of 3-ketodigoxigenin conjugate of malate dehydrogenase A. A clear solution of 3-ketodigoxigenin (228, mg, 0.59 mmoles), carboxymethoxylamine hemihydrochloride (140 mg, 0.64 mmole) and sodium acetate (294 mg, 3.6 mmole) in methanol (18 ml, dried over molecular sieves 3A) was refluxed under nitrogen for 3 hours. The tlc of an aliquot of a sample showed the complete formation of the oxime derivative ($R_f$ 0.33; 0.5:1:10/HOAc-MeOH-CHCl$_3$, silica gel plate). The resulting reaction product was stripped to dryness, the residue dissolved in 32 ml 5% $NaHCO_3$ at 5°–10°, and was extracted with 3×20 ml chloroform. The chloroform extracts were discarded. The bicarbonate layer was acidified at 5°–10° with 28 ml of 1 N hydrochloric acid to pH 2–3 and was extracted with 10×25 ml ethyl acetate. The ethyl acetate extracts were washed with saturated sodium chloride and dried over anhydrous sodium sulfate. Evaporation of the solvent gave a solid which recrystallized from a mixture of methanol-ethyl acetate-hexane. The while solid [188 mg, mp. 202°–220° (dec)], was carboxymethoxyoximino 3-ketodigoxigenin,.

B. MDH (1.0 ml, 10 mg/ml suspended in $(NH_4)_2SO_4$) was put into a Brinkman centrifuge tube and centrifuged for 4 minutes. The supernatant was discarded and the precipitate was dissolved in 1.5 ml of 0.05 M $CO_3/HCO_3$ buffer (424 mg. $Na_2CO_3$, 3.864 gm $NaHCO_3$ in 1.0 l. deionized $H_2O$, pH 9.2). This was then dialyzed against the same $CO_3/HCO_3$ buffer. After the dialysis, the protein concentration was 6.02 mg/ml MDH.

C. Dry carboxymethyl oxime of digoxigenin (prepared above) (23.05 mg, 0.05 m mole) was placed in a carefully dried flask fitted with a serum stopper and a drying tube, and a 250 μl aliquot of DMF (dried over 4 Å molecular sieves) and a 7.1 μl (0.052 mmole) of triethylamine (stored over KOH) were added through the serum stopper with a syringe while stirring at room temperature. The reaction flask was then cooled to −14° with a salt-ice bath. Then, 9.3 μl (0.05 mmole) of carbitol chlorformate was added below the surface of the DMF solution. This mixture was allowed to stir for thirty minutes before proceeding with the conjugation.

D. MDH (6.02 mg/ml in 0.05 M $CO_3/HCO_3$ buffer pH 9.2) (see above) was put into a reaction vial fitted with a 7 mm stirring bar and cooled to 0°, while the mixed anhydride was kept stirring at −14°. The mixed anhydride was removed with a syringe through the serum stopper 1 μl at a time and added to the enzyme at a rate of 1 μl per minute. Activity and inhibition checks were made after the addition of 3 μl of mixed anhydride and after 6 μl of mixed anhydride. The percent inhibition was determined by adding 5 μl of full strength antidigoxin along with the buffer, substrate and enzyme. At this point (0.5% deactivation and 68.8% inhibition) a 0.4 ml aliquot was removed and dialyzed against 0.05 M $CO_3/HCO_3$ buffer.

Addition of mixed anhydride was continued and activity and inhibition checks were made after a total of 10 μl and 20 μl of mixed anhydride had been added. At this point (50.0% deactivation and 81.2% inhibition), the remaining enzyme was dialyzed against 0.05 M $CO_3/HCO_3$ buffer.

Assays

In order to demonstrate the use of malate dehydrogenase as the enzyme in homogeneous enzyme immunoassays, a number of assays were carried out in addition to those previously described in the experimental section.

An extensive clinical study was carried out in developing a urine cannabinoid assay. The following reagents were employed:

Antibody reagent: 0.1 M NAD, 0.153 M glycine, 0.2% gelatin, 0.01% $NaN_3$ and antibody to $\Delta^9$-THC prepared using the 9-formyl-$\Delta^9$-THC reductive amination product with BSA.

Enzyme Reagent: MDH conjugate prepared in accordance with the procedure of Example VII and purified through a Sephadex G-25 (94×2.6 cm) column. (The Sephadex G-25 was swelled 24 hrs. in 1 M propionic acid, then packed, washed with 500 ml 1 M propionic acid, 500 ml water, and then 1.0 l. of 0.5 M $PO_4$-2.7×10$^{-4}$M EDTA buffer, pH 7.6. Chromatography performed in the cold with the above buffer at a flow rate of ~6 drops/min and 90 drop fractions collected. Fractions were assayed and the peak tubes pooled (21.3 ml). Final concentration 1.14 mg protein/ml. The enzyme retained 27% of the original activity and was 59% inhibited. Sodium azide was added to give a 0.01% solution.

The purified enzyme solution was diluted 1:163 in an aqueous solution containing 30% glycerol, 0.5 M $KH_2PO_4$, 0.07% Triton X 405, 0.01% EDTA and 0.01% $NaN_3$.

Calibrations: Negative urine was employed to prepare samples having known amounts of 11-nor-$\Delta^9$-THC-9-carboxylic acid. The aforementioned acid (1.448 mg) was dissolved in 1.93 ml DMF to provide a concentration of 750 μg/ml and then added to the urine to provide concentrations of 15 μg/ml; 25 μg/ml; and 75 μg/ml. The solutions were then lyophilized and stored in sealed containers.

Buffer: 0.1 M glycine, 0.375 M $K_2HPO_4$, 0.143 M l-malate, 0.01% EDTA and 0.01% $NaN_3$, pH 9.75.

The assay protocol was as follows:

(1) Deliver 50 μl of sample or calibrator and 250 μl of buffer to a 75×100 mm testube.

(2) Deliver 50 μl of antibody reagent and 250 μl of buffer to the same tube.

(3) Deliver 50 μl of enzyme reagent and 250 μl of buffer to the same tube.

(4) Vortex mix the combined solution while clearing the thermostatted, 30°, flor cell of a Gilford Stasar III spectrophotometer set in the "concentration" mode where Con = 2×A.

(5) Aspirate the solution into the flow cell and read the enzyme rate during a 60 second interval following a 13 second delay for temperature equilibration.

On the first day of the clinical study, 12 subjects did not receive any drug. On the second to fifth day, the subjects were given at noon each day, either a placebo cigarette or one spiked with 10 mg or 20 mg of $\Delta^9$-THC. The total urine excreted by the subjects over the five day period was collected in four equal six hour portions per day. Urine creatinine was determined for each sample and the physiological effects of the drugs on the subjects was monitored. A sample was considered negative if the assay value for cannabinoids was less than 15 ng/ml, the cutoff calibrator for 25 ng/ml detection.

The conclusions which were drawn from the data were that the assay was always successful in picking out negative subjects, with two exceptions which were explainable for other reasons. A 20 mg dose was always detected. A 10 mg dose was not always detected. However, the spiked cigarettes had been stored for some time under non-ideal conditions and could, therefore, have lost some of their potency. Only two apparent false positives were obtained.

In the assay for triiodothyronine ($T_3$), the conjugate employed was prepared in accordance with Example XI and 3.5 $T_3$ groups were added; the percent of the original activity of the enzyme was 64.9 and inhibitability was 48.5%. The antibody employed had been prepared in reference to the diglycolic amide of $T_3$ conjugated to bovine gamma globulin in accordance with conventional procedures. Enzyme activity in the presence of antibody and $T_3$ was determined as follows.

Into a 1 cm half length cuvette was introduced 0.1 ml $T_3$ in 0.05 N NaOH plus 0.6 ml of 0.1 M glycine-111 mM malate, 0.1% RSA and 0.01% EDTA, pH 9.54; 0.1 ml 0.1 M NAD (pH 5) in 0.3 ml of glycine buffer (see above); 0.05 ml antibody or trisbuffer (50 mM tris-HCl plus 1% KCl plus 1 mM $N_3$, pH 7.56). The mixture was incubated at 30° for 5.6 minutes. To the mixture was then added 0.05 ml of the conjugate diluted from the preparation $3.3 \times 10^4$ fold to provide an enzyme concentration affording a convenient enzyme rate and 0.6 ml of glycine buffer and the solution mixed by triple inversion of the cuvette. After incubating at 30° for 10.4 minutes, the initial OD at 340 nm in a Bausch & Lomb Spectronic 100 was determined and recorded. The mixture was then incubated for an additional 40 minutes at 30° and the final OD recorded at 340 nm. The dose response curve for varying values of $T_3$ is as follows:

TABLE

| $T_3$ Conc. M $\times 10^{11}$ | O.D. at 340 nm |
|---|---|
| 1.2 | .263 |
| 3.6 | .270 |
| 11 | .277 |
| 27 | .298 |
| 44 | .317 |
| 110 | .333 |

It is evident from the above results, that $T_3$ can be determined in the assay medium at extremely low concentrations. The assay with malate dehydrogenase conjugate is able to detect molar concentrations at levels of $10^{-11}$.

The use of malate dehydrogenase as the enzyme in homogeneous enzyme immunoassays has a number of substantial advantages. The enzyme has a high turnover rate and is stable in storage under moderate conditions for long periods of time. The enzyme can be conjugated to a wide variety of haptens, whereby the conjugate retains a substantial proportion of the original activity of the enzyme, while at the same time upon binding to antibody, the enzyme can be substantially inhibited. This allows for excellent sensitivity since small changes in the amount of antibody binding to the enzyme results in significant changes in the enzyme activity. Furthermore, the enzyme uses NAD, which allows for an easy and accurate spectrophotometric assay employed generally available equipment. Excellent reproducibility can be achieved. In addition, the enzyme is found not be sensitive to a wide variety of components which are found in physiological fluids which are of interest to be assayed.

Although the foregoing invention has been described in some detail by way of illustration and example for purposes of clarity of understanding, it will be obvious that certain changes and modifications may be practiced within the scope of the appended claims.

What is claimed is:

1. An enzyme conjugate of malate dehydrogenase bonded to on the average with from about 1 to 18 haptens of molecular weight of from about 125 to 1,200 and having at least one heteroatom, wherein said conjugated enzyme retains at least about 2% of the original enzyme activity prior to conjugation and wherein the enzymatic activity of the conjugate is reduced by at least 30% when said haptens are bound to antibodies for said haptens.

2. An enzyme conjugate of malate dehydrogenase of the formula:

MDH (X—R—Y)$_n$ wherein:

MDH intends malate dehydrogenase;

n is on the average in the range of 1 to 18;

R is a bond, a hydrocarbon linking group of from 1 to 8 carbon atoms or a substituted hydrocarbon linking group of from 1 to 8 carbon atoms and from 0 to 3 heteroatoms which are oxygen, nitrogen and sulfur;

X is a bond, a non-oxocarbonyl group, including the nitrogen and sulfur analogs thereof or diazo, when bonded to an aromatic annular carbon atom; and Y is a hapten of from about 125 to about 1,000 molecular weight and having at least one heteroatom.

3. An enzyme conjugate according to claim 2, wherein n is of from two to 12, X is a non-oxocarbonyl group, R is of from 1 to 4 carbon atoms and 0 to 2 heteroatoms, and Y is a hapten of from about 125 to about 650 molecular weight.

4. An enzyme conjugate according to claim 2, wherein said malate dehydrogenase is derived from heart.

5. An enzyme conjugate of the formula

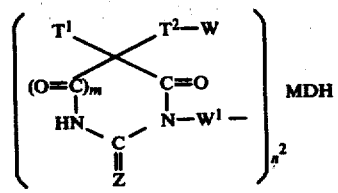

wherein:

$n^2$ is on the average in the range of 1 to 14;

$T^1$ and $T^2$ are hydrocarbon of from 1 to 7 carbon atoms and 0 to 1 site of aliphatic unsaturation and are both phenyl when m is 0;

one of W and $W^1$ is —$R^2$—$X^2$— and the other is hydrogen;

Z is oxygen or $H_2$;

m is 0 or 1;

$R^2$ is an aliphatic group of from 1 to 8 carbon atoms and 0 to 3 heteroatoms having from 0 to 1 site of aliphatic unsaturation, wherein the heteroatoms are oxygen, sulfur and nitrogen or aromatic hydrocarbon of from 6 to 9 carbon atoms; and $X^2$ is a bond, non-oxocarbonyl including the nitrogen and thioanalogs thereof or diazo when bounded to an aromatic annular carbon atom.

6. An enzyme conjugate according to claim 5 wherein m is 0 and $T^1$ and $T^2$ are phenyl.

7. An enzyme conjugate according to claim 5, wherein m is 1, Z is oxygen, $R^2$ is of from 1 to 6 carbon atoms and from 0 to 2 heteroatoms and $X^2$ is non-oxocarbonyl.

8. An enzyme conjugate according to claim 7, wherein $Z^2$ is oxygen.

9. An enzyme conjugate of the formula

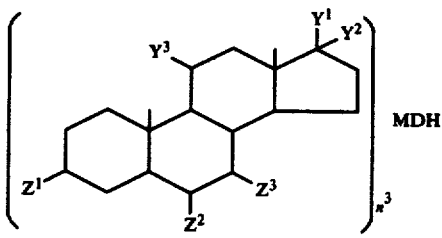

wherein:
$n^3$ is on the average in the range of 1 to 14;
one of $Z^1$, $Z^2$ and $Z^3$ is —$R^3$—$X^3$—, wherein $R^3$ may be singly or doubly bonded to the annular carbon atom, and $R^3$ is an aliphatic group of from 1 to 8 carbon atoms and 0 to 3 heteroatoms, which are oxygen, sulfur or nitrogen, or aromatic hydrocarbon of from 6 to 9 carbon atoms;
when other than —$R^3$—$X^3$—, $Z^2$ and $Z^3$ are hydrogen;
$X^3$ is a bond, non-oxocarbonyl including the nitrogen and sulfur analogs thereof or, when $R^3$ is aromatic hydrocarbon, diazo;
with the proviso that when the steroid is a gestogen, there is from 0 to 1 site of ethylenic unsaturation in the $\Delta^4$ or $\Delta^5$ position; and
when other than —$R^3$—$X^3$—, $Z^1$ is hydroxyl or oxo;
$Y^1$ is acetyl; and
$Y^2$ and $Y^3$ are hydrogen;
when the steroid is an androgen, when other than —$R^3$—$X^3$—,
$Z^1$ is oxo;
$Y^1$ is hydroxyl; and
$Y^2$ and $Y^3$ are hydrogen; and
when the steroid is an adrenocortical hormone, when other than —$R^3$—$X^3$—, $Z^1$ is oxo;
$Y^1$ is hydroxyacetyl;
$Y^2$ is hydrogen or hydroxyl; and
$Y^3$ is hydroxy or oxo.

10. An enzyme conjugate according to claim 9, wherein $Z^2$ and $Z^3$ are hydrogen and $Y^1$ and $Y^2$ are taken together to define oxo.

11. An enzyme conjugate according to claim 9, wherein $Y^2$ and $Y^3$ are hydrogen and $Y^1$ is hydroxyl.

12. An enzyme conjugate of the formula

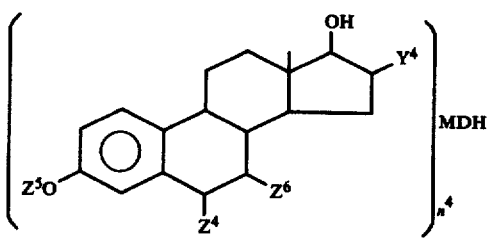

wherein:
one of $Z^4$, $Z^5$ and $Z^6$ is —$R^4$—$X^4$—, wherein when $Z^4$ or $Z^6$ is —$R^4$—$X^4$—, $R^4$ may be singly or doubly bonded to the annular carbon atom and wherein $R^4$ is an aliphatic radical of from 1 to 8 carbon atoms, and from 0 to 3 heteroatoms, which are oxygen, nitrogen and sulfur, or aromatic hydrocarbon of from 6 to 9 carbon atoms;
$X^4$ is a bond, non-oxocarbonyl including the nitrogen and sulfur analogs thereof or, when $R^4$ is aromatic hydrocarbon, diazo;

when other than —$R^4$—$X^4$—, $Z^4$, $Z^5$ and $Z^6$ are hydrogen;
$Y^4$ is hydrogen or hydroxyl; and
$n^4$ is on the average in the range of from 1 to 14.

13. An enzyme conjugate of the formula

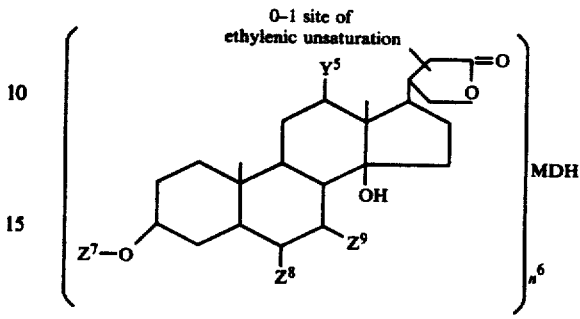

wherein:
one of $Z^7$, $Z^8$, and $Z^9$ is —$R^6$—$X^6$—, wherein when $Z^8$ or $Z^9$ is —$R^6$—$X^6$—, $R^6$ may be singly or doubly bonded to the annular carbon atom;
$R^6$ is an aliphatic radical of from 1 to 8 carbon atoms and 0 to 3 heteroatoms having from 0 to 1 site of aliphatic unsaturation, wherein said heteroatoms are oxygen, sulfur or nitrogen, or a mono- or disaccharide residue modified for linking to an amino group;
$X^6$ is non-oxocarbonyl including the nitrogen and sulfur analogs thereof or a bond;
when other than $R^6$—$X^6$—, $Z^{7-9}$ are hydrogen;
$Y^5$ is hydrogen or hydroxyl; and
$n^6$ is on the average in the range of from about 1 to 14.

14. An enzyme conjugate of a formula:

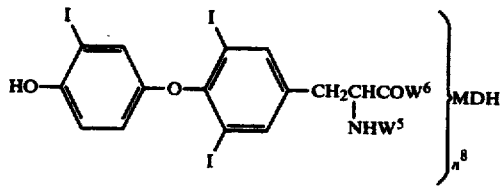

wherein:
one of $W^5$ and $W^6$ is —$R^8$—$X^8$—;
$R^8$ is an aliphatic group of from about 2 to 10 carbon atoms having from 0 to 2 heteroatoms which are oxygen and nitrogen and from 0 to 1 site of aliphatic unsaturation;
$R^8$ is a bond or nonoxocarbonyl, including the nitrogen and sulfur analogs thereof;
when other than —$R^8$—$X^8$—,
$W^5$ is hydrogen and $W^6$ is hydroxyl, alkoxy of from 1 to 3 carbon atoms or amino; and
$n^8$ is on the average in the range of from about 1 to 14.

15. A testosterone conjugate to malate dehydrogenase linked at the 3 position having from about 1 to 14 testosterone groups.

16. An estradiol conjugate to malate dehydrogenase linked at the 3 position having from about 1 to 14 estradiol groups.

17. A triiodothyronine conjugate to malate dehydrogenase, linked at the amino group having from about 1 to 14 triiodothyronine groups.

18. A digoxigenin conjugate to malate dehydrogenase linked at the 3 position having from about 1 to 14 digoxigenin groups.

* * * * *